United States Patent
Schnitzler

(10) Patent No.: US 9,326,811 B2
(45) Date of Patent: May 3, 2016

(54) SWITCHING CONTROL DEVICE AND MANIPULATING PART FOR A MEDICAL INSTRUMENT

(75) Inventor: Uwe Schnitzler, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 738 days.

(21) Appl. No.: 13/256,174

(22) PCT Filed: Mar. 10, 2010

(86) PCT No.: PCT/EP2010/001490
§ 371 (c)(1),
(2), (4) Date: Sep. 12, 2011

(87) PCT Pub. No.: WO2010/102800
PCT Pub. Date: Sep. 16, 2010

(65) Prior Publication Data
US 2012/0004649 A1 Jan. 5, 2012

(30) Foreign Application Priority Data

Mar. 12, 2009 (DE) .......... 10 2009 012 910
Mar. 5, 2010 (DE) .......... 10 2010 000 642

(51) Int. Cl.
*A61B 18/14* (2006.01)
*A61B 19/00* (2006.01)

(52) U.S. Cl.
CPC ..... *A61B 18/1402* (2013.01); *A61B 2019/4868* (2013.01)

(58) Field of Classification Search
USPC .......................................... 606/45
See application file for complete search history.

(56) References Cited

U.S. PATENT DOCUMENTS

| 4,552,143 | A | * | 11/1985 | Lottick | .......................... 606/42 |
| 4,596,335 | A | * | 6/1986 | Hull | .......................... 211/69.1 |
| 5,433,702 | A | * | 7/1995 | Zelman | ............... A61F 9/00745 200/295 |
| 6,071,281 | A | | 6/2000 | Burnside et al. | |
| 6,623,500 | B1 | | 9/2003 | Cook et al. | |
| 8,226,237 | B2 | * | 7/2012 | Mandelstam-Manor et al. | ............................. 351/222 |
| 2006/0217700 | A1 | | 9/2006 | Garito et al. | |

FOREIGN PATENT DOCUMENTS

| CN | 2649033 Y | 10/2004 |
| CN | 201088624 Y | 7/2008 |
| DE | 24 60 481 A1 | 6/1976 |
| DE | 298 10 996 U1 | 9/1998 |

(Continued)

OTHER PUBLICATIONS

Written Opinion from PCT/EP2010/001490.

*Primary Examiner* — Paula J Stice
(74) *Attorney, Agent, or Firm* — Blank Rome LLP

(57) ABSTRACT

A switching control device for a medical instrument such as an electrode used in high frequency (HF) surgery. The switching control device comprises a connection line, designed as a switching control module for controlling various electrical operating modes of the instrument with a three-dimensionally and pressure-tightly sealed housing that is resistant to sterilization temperatures, an actuating element and fixing means to be releasably mounted within or on a manipulating part of the instrument, and module contacting means for interacting with device- or instrument-contacting means that are connected to the connection line to perform a switching control function.

21 Claims, 2 Drawing Sheets

(56) References Cited

FOREIGN PATENT DOCUMENTS

| | | | |
|---|---|---|---|
| DE | 198 54 313 A1 | 6/2000 | |
| DE | 601 32 690 T2 | 3/2009 | |
| EP | 1 199 040 A2 | 4/2002 | |
| JP | 2000-126202 A | 5/2000 | |
| JP | 2002-177295 A | 6/2002 | |
| JP | 2006-271968 A | 10/2006 | |
| WO | WO 2007/005507 A2 | 1/2007 | |
| WO | WO 2008/152378 A2 | 12/2008 | |

* cited by examiner

SWITCHING CONTROL DEVICE AND MANIPULATING PART FOR A MEDICAL INSTRUMENT

CROSS-REFERENCE TO RELATED APPLICATIONS

This application is the U.S. national stage of International Application No. PCT/EP2010/01490, filed Mar. 10, 2010, which claims priority to German application no. 10 2009 012 910.3, filed Mar. 12, 2009 and German application no. 10 2010 000 642.4, filed Mar. 5, 2010, the entire disclosures of which are all incorporated by reference herein.

FIELD OF THE INVENTION

Embodiments of the invention relate to a switching control device for a medical instrument, especially an electrode for HF surgery, and a manipulating part for an instrument of this type.

BACKGROUND

Hereinafter, the term "switching control device" denotes any switch and/or control device(s) with which an operator can switch, or control in some other way (including in an analog way) a function of the instrument in question, especially an energy supply thereto, a geometric configuration thereof or a signal transmission there-from. An "instrument" should be understood to mean any medical—surgical, therapeutic or diagnostic—instrument and "manipulating part" denotes parts or sections of an instrument of this kind, which an operator holds in the hand and/or on which he/she performs switching or control functions when the instrument is used for medical purposes.

The reusable surgical manipulating elements having an activation function (e.g., electrode handles for HF surgery) currently available on the market are designed such that the switching function or the electronic components required therefore (such as, e.g., push buttons, resistances, diodes) are mounted on a printed circuit board, which is integrated centrally in the interior of the handles.

The electrical cable connections (litz wires) are usually soldered onto the printed circuit board. The contact socket required for the electrical and mechanical contacting of the instruments (e.g., monopolar electrodes) is also attached to the printed circuit board (e.g., by soldering). In the case of HF surgery handles, the power required for use is thus supplied via the conductors mounted on the printed circuit board.

Surgical manipulating elements with an activating function (e.g., electrode handles for HF surgery) are prepared by sterilization using moist heat, ethylene oxide gas or gamma radiation. It is necessary to ensure that the products fulfill their function over a defined period without any restriction and that no safety-relevant defects posing a risk to the patient and user occur thereby. The ambient conditions (thermal, physical) of the different sterilization methods can result in the premature failure of the products, e.g., due to the penetration of fluids.

To maintain a fault-free function and exclude safety-relevant defects, it is necessary to prevent the penetration of moisture (initiated by preparation: washing, sterilization). This is generally achieved by mechanical seals (e.g., O-rings) at the interfaces to the external environment (e.g., cable outlet, button region, contact socket region on the distal end of the handle).

The structural principles of the activating function for different surgical manipulating elements can sometimes differ greatly and consequently, the maintenance of the defined lifetime in accordance with the safety requirements can turn out very differently.

The known solutions to prevent the penetration of moisture during the preparation, washing or sterilization of the instruments or manipulating parts have certain systemic drawbacks:

Mechanical sealing of the numerous interfaces is difficult to achieve, especially due to material changes induced by chemical/thermal reconditioning. The sealing elements are exposed to extreme stress due to the "tight system" and trapped air (in large hollow spaces), thermal cycling and the corresponding gas exchange in the interior of the handles (initiated by the washing and sterilization processes). The penetration of moisture can cause corrosion of metallic parts (especially conductors, contacts, connections between electronic components), which can result in a functional failure and, in the "worst case," to self-activation. Especially with HF conducting structures, the penetration of moisture can result in corrosion initiated by electrochemical processes, which can have extremely serious consequences from both functional and safety viewpoints.

SUMMARY

It is an object of the embodiments of the invention to resolve the problems of known manipulating parts using a new concept, which especially facilitates the provision of manipulating parts with unrestricted functions and the satisfaction of all safety requirements over a required lifetime while also achieving improvements with respect to the ease of production and process reliability of the manipulating parts.

This object is achieved according to a first aspect by a novel switching control device for medical instruments with the features described herein and according to a second aspect by a manipulating part described herein. Also provided is a set of medical instruments with corresponding manipulating parts.

Embodiments of the invention include the concept of a modular implementation of the actual manipulation function and the switching control function(s) of instruments of the type described herein. This modularity is such that the switching control device is designed as a relatively independent, inherently three-dimensionally enclosed switching control module with the corresponding actuating element and communication means for interacting with the instrument or an associated device for implementing the switching/control function. The embodiments of the invention also include providing fixing means to be releasably mounted within, or on, the manipulating part on this switching control module. Moreover, the switching control module is designed to be pressure-tight and insensitive to heat such that it reliably withstands the prevailing ambient conditions during washing, sterilization, etc. over numerous application cycles.

The switching control module does not have its own electrical supply lead; instead, it engages its contacting means in internal electrical connections of an instrument, which can be connected via an instrument supply lead to the power network.

A significant advantage of the proposed solution consists in the fact that, due to the small physical size, the residual gas content in the switching control module can be kept very low and the stress on the parts (especially the housing) due to thermal cycling can be significantly reduced. The manipulating parts remaining after the removal of the switching control module do not have to have a tight design (i.e., the aforementioned, structurally and technologically complex sealing of interfaces is no longer necessary). This results in a simple and reliable assembly technology for the novel, modular manipulating parts.

In a preferred embodiment, the switching control module can be used in a "standardized" design, if necessary, in a plurality of different, but system-compatible manipulating parts or instruments—and optionally also as an independent unit, without spatial reference to a manipulating part. This facilitates further simplifications of the design and production processes and logistics in the hospital or surgery.

In an embodiment that offers a wide range of possible applications from the current viewpoint, the module contacting means comprises plug-in contact elements, especially contact pins or a plug, for engagement in connection contacts of the manipulating part. Alternatively, the module's contacting means can comprise a wireless transmission unit, especially a Bluetooth™, IR or ultrasound transmission unit. In particular, the embodiment also facilitates a stand-alone function of the switching control device, spatially detached from a manipulating part in the narrower sense.

In a further embodiment, the fixing means comprises latching means, which are especially molded onto the housing. Alternatively or in combination with, the fixing means can comprise a threaded section, which is especially molded onto the housing. It is also possible to use additional simple fixing or connecting means in a manner known for the production of a releasable connection between the switching control module and the manipulating part (for example, means such as bayonet locks, sliding guides etc.).

In a particularly expedient embodiment, the actuating element can be formed from a deformable section of the housing. For example, in the case of a switching control device comprising a push button as an activating element, a switching spring molded into the housing of the push button, which simultaneously forms the housing of the switching control module, can form the actuating element.

Expedient features of the manipulating part according to the embodiments of the invention may be derived from the above statements relating to the embodiment of the switching control module and, therefore, they will not be repeated here. Overall, it is understood that handle-side fixing or connecting means and contacting means are designed to correspond to the corresponding fixing or contacting means of the switching control module. Where functionally possible, it is also possible to interchange features, for example, to provide contact pins in the handle and corresponding contact sockets on the switching control module. It should be noted that endoscopic instruments with no manipulating part in the narrower sense, but which can be guided and switched/controlled by an operator are expressly considered to belong within the scope of the disclosed embodiments of the invention.

BRIEF DESCRIPTION OF THE DRAWINGS

The aforementioned advantages and expedient features can also be derived from the following description of exemplary embodiments and aspects of the invention with reference to the drawings, in which.

DETAILED DESCRIPTION

Figure 1A:
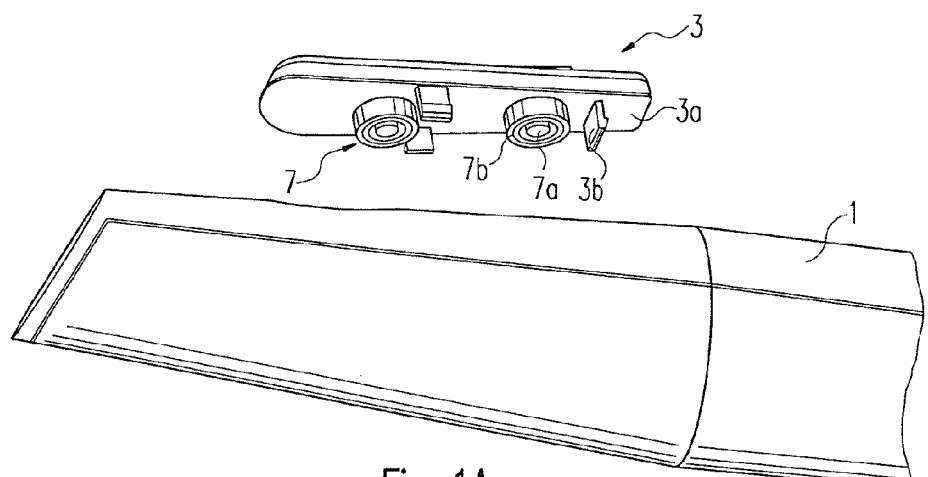
FIGS. 1A to 1C are perspective views of a manipulating part according to an embodiment of the invention with a removable switching control module.
Figure 1B:
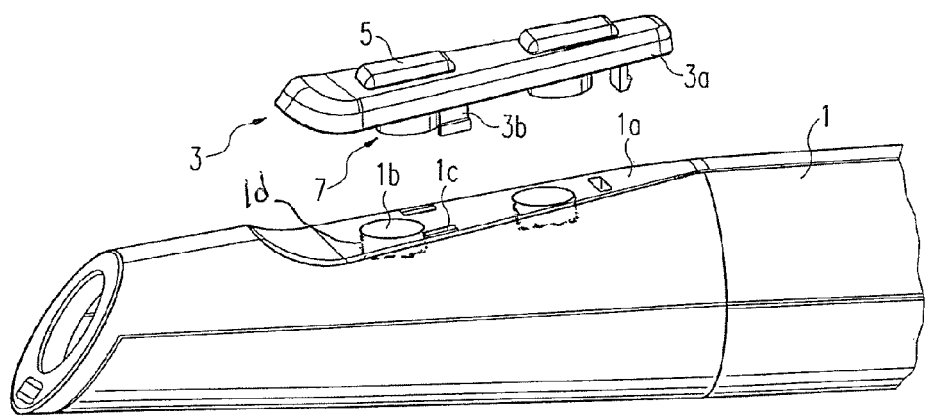
Figure 1C:
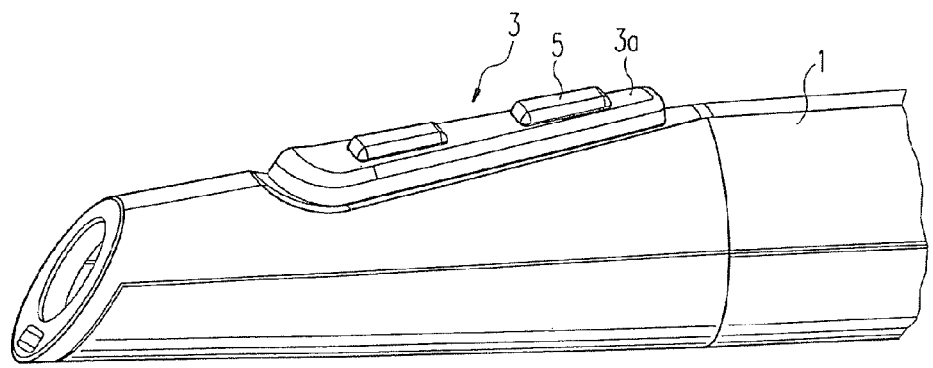

FIGS. 1A to 1C show a manipulating part (e.g., as an HF electrode handle) 1 to guide an HF electrode (not shown) for HF surgery containing a removable switching control module 3. The switching control module 3 has a housing 3a with a molded-on latching hook 3b and two push buttons 5 as actuating elements for each on/off switch 7 used in the housing 3a. The switches are used for switching between various (electrical) operating modes of the instrument. It should be noted that it is also possible to provide rotating or sliding actuators for controlling electrical operating parameters of the instrument instead of one or both switches.

Each switch 7 has ring-shaped inner and outer contacts 7a, 7b. Provided on the manipulating part 1, there is a bevelled surface section 1a for mounting the switching control module 3; in this section, there are first recesses 1b, which can accommodate the switch 7 and have contacts 1d for engaging switch 7 and contacts 7a, 7b, and second recesses 1c, which interact as fixing or latching means on the handle side with the latching hook 3b on the switching control modules.

Figure 2:
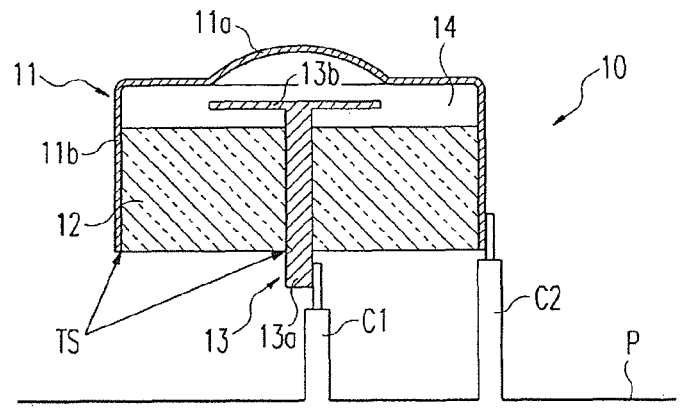
FIG. 2 illustrates a longitudinal section of a push button as a component of the switching control module shown in FIGS. 1A to 1C.

FIG. 2 shows a push button 10 connected to two external connection contacts C1, C2 arranged on a printed circuit board P of a medical manipulating part. The push button 10, which, in the embodiment of the invention shown in FIGS. 1A to 1C, can be used instead of the switch 7, comprises a first housing piece 11 in the shape of a pot with a floor (that includes dent 11a) in the shape of a spherical segment and a cylindrical wall 11b, a ring-shaped second housing piece 12 made of glass and a contact piece (mating contact) 13 placed centrically in the glass housing piece 12. The dimensions of the outer diameter of the second housing piece are selected so that it fits in the cylindrical wall 11b of the first housing piece 11 with virtually no play, and a pin portion 13a of the contact piece 13 fits in the cylindrical bushing in its center, again with virtually no play.

A thermal machining step creates in each case a hermetically tight sealing TS on the contact surfaces of the parts mentioned above. The contact piece 13 is placed in the push button 10 such that a circular contact plate 13b comes to lie on its inner end in a hollow space 14 between the internal face of the second housing piece 12 and the floor of the first housing piece 11, and, to be precise, with a spacing below the dent 11a in the floor of the first housing piece such that, on elastic depression, it touches the contact plate 13b. This establishes a (temporary) electrical connection between the connecting contact C1, to which the contact piece 13 is connected, and the connecting contact C2, to which the conductive first housing piece 11 is connected. Thus, the dent 11a serves as a switching spring of the push button 10 and, in a modification of the embodiment according to FIGS. 1A to 1C, can directly replace the actuating push button or be arranged there-under.

Figure 3:
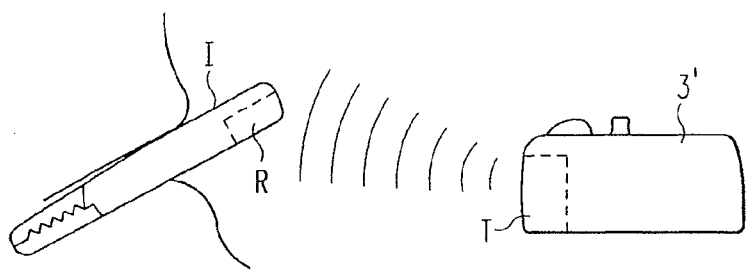
FIG. 3 is a sketch of a further embodiment of the invention.

FIG. 3 shows a further embodiment of a switching control module 3', which (in another configuration) can be connected to a manipulating part of a medical instrument, but, in the configuration shown, is not integrated into a handle; instead, it is manipulated by the operator independently to execute control functions on an endoscopic instrument I. The signal connection takes places over a wireless link and, to this end, the switching control module 3' comprises a wireless transmission unit T and the instrument I comprises a corresponding receiver unit R. Wireless transmission unit T may be, for example, a Bluetooth™, IR or ultrasound transmission unit.

Figure 4:
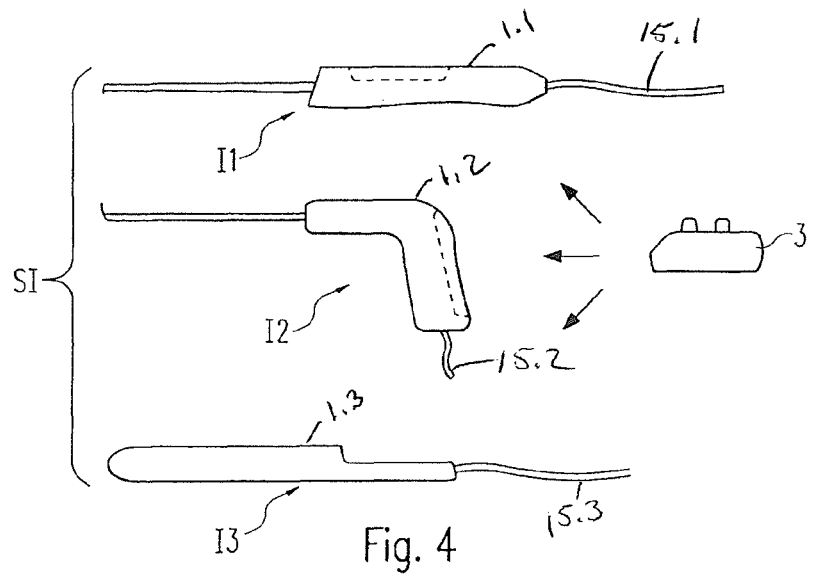
FIG. 4 is a sketch of a set of medical instruments designed according to the embodiments disclosed herein.

FIG. 4 is a sketch of a set SI of medical instruments I1 to I3 with differently designed manipulating parts 1.1 to 1.3, each comprising a fixed connection line 15.1 to 15.3 and uniformly designed receptacles for a switching control module 3. Thus, each instrument can be fitted with the same switching control unit, or only one single type of switching control device needs to be produced for all instruments and kept in store.

The embodiments of the invention are not restricted to the examples described and aspects highlighted above; instead, a plurality of modifications within the scope of professional practice may be made.

The invention claimed is:

1. A reusable switching control device for a medical instrument configured to receive power from an HF power supply, said reusable switching control device comprising:
  an actuating element for controlling operation of the medical instrument; and
  device contacting means for communicating with the instrument via instrument contacting means that are connected to a connection line for providing to the medical instrument at least one selected from the group of power and signal transmission, the device contacting means having inbound and outbound connections to the HF power supply via the instrument.

2. The reusable switching control device of claim 1, wherein the device contacting means comprises plug-in contact elements for engagement with connection contacts of the medical instrument.

3. The reusable switching control device of claim 1, wherein the device contacting means comprises contact pins or a plug for engagement with connection contacts of the medical instrument.

4. The reusable switching control device of claim 1, further comprising fixing means for releasably attaching the reusable switching control device to a manipulating part of the instrument.

5. The reusable switching control device of claim 4, wherein the fixing means comprises latching means molded onto the housing.

6. The reusable switching control device of claim 4, wherein the fixing means comprises a threaded section molded onto the housing.

7. The reusable switching control device of claim 1, wherein the actuating element is a push button.

8. The reusable switching control device of claim 1, wherein the actuating element comprises a pressure-deformable section of the housing.

9. The reusable switching control device of claim 1, wherein the reusable switching control device is configured to receive power from the connection line via the device contacting means and the instrument contacting means.

10. The switching control device of claim 1, wherein the reusable switching control device is pressure-tightly sealed and resistant to sterilization temperatures.

11. A medical instrument comprising:
  a connection line for connecting the medical instrument to an HF power supply and for providing power to the medical instrument; and
  a manipulating part comprising instrument contacting means connected to the connection line and for communicating with a reusable switching control device, said reusable switching control device comprising:
  an actuating element for controlling operation of the medical instrument; and
  device contacting means for communicating with the instrument via the instrument contacting means, the device contacting means having inbound and outbound to the HF power supply via the medical instrument.

12. The medical instrument of claim 11, wherein the device contacting means comprises connection contacts for engaging plug-in contact elements of the reusable switching control device.

13. The medical instrument of claim 11, wherein the manipulating part further comprises latching means designed to correspond to corresponding fixing means of the reusable switching control device.

14. The medical instrument of claim 13, wherein the latching means comprises a threaded section designed to correspond to a corresponding threaded section of the fixing means.

15. The medical instrument of claim 11, wherein the reusable switching control device is pressure-tightly sealed and resistant to sterilization temperatures.

16. The medical instrument of claim 11, wherein the reusable switching control device is configured to receive power from the connection line via the device contacting means and the instrument contacting means.

17. A set of medical instruments, each medical instrument comprising:
  a connection line for connecting the medical instrument to an HF power source and for providing power to the medical instrument; and
  a manipulating part comprising instrument contacting means connected to the connection line and for communicating with a reusable switching control device, said reusable switching control device comprising:
  an actuating element for controlling operation of the medical instrument; and
  device contacting means for communicating with the instrument via the instrument contacting means, the device contacting means having inbound and outbound to the HF power source via the respective medical instrument.

18. The set of medical instruments of claim 17, wherein each medical instrument is configured to communicate with a different reusable switching control device.

19. The set of medical instruments of claim 17, wherein each medical instrument is configured to communicate with the same reusable switching control device.

20. The set of medical instruments of claim 17, wherein the reusable switching control device is pressure-tightly sealed and resistant to sterilization temperatures.

21. The set of medical instruments of claim 17, wherein the reusable switching control device is configured to receive power from the connection line via the device contacting means and the instrument contacting means.

* * * * *